(12) United States Patent
Dromms et al.

(10) Patent No.: US 6,783,500 B2
(45) Date of Patent: Aug. 31, 2004

(54) HAND-HELD BLOOD PRESSURE MEASURING APPARATUS

(75) Inventors: Raymond P. Dromms, Liverpool, NY (US); Robert L. Vivenzio, Auburn, NY (US); John W. Sims, Weedsport, NY (US); Thomas J. Grant, Skaneateles, NY (US); Scott W. Osiecki, Skaneateles, NY (US); Staci A. Mininger, Dallas, TX (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 74 days.

(21) Appl. No.: 10/050,490

(22) Filed: Jan. 16, 2002

(65) Prior Publication Data

US 2003/0135123 A1 Jul. 17, 2003

(51) Int. Cl.[7] .................................. A61B 5/00
(52) U.S. Cl. ....................... 600/490; 600/499
(58) Field of Search .................. 600/450, 493–6

(56) References Cited

U.S. PATENT DOCUMENTS

| | | | | |
|---|---|---|---|---|
| 3,613,667 A | * | 10/1971 | Beck | 600/494 |
| 3,896,791 A | * | 7/1975 | Ono | 600/493 |
| 3,906,939 A | * | 9/1975 | Aronson | 600/493 |
| D250,128 S | * | 10/1978 | Miyazawa | 600/494 |
| 4,248,242 A | * | 2/1981 | Tamm | 600/493 |
| 4,459,991 A | * | 7/1984 | Hatschek | 600/493 |
| 4,552,153 A | | 11/1985 | Newman et al. | |
| D284,508 S | * | 7/1986 | Enatsu | 600/493 |
| D286,070 S | * | 10/1986 | Moro | 600/494 |
| 5,669,390 A | * | 9/1997 | McCormick et al. | 600/499 |
| 5,966,829 A | | 10/1999 | Lia et al. | |
| 6,036,718 A | | 3/2000 | Ledford et al. | |
| 6,120,458 A | | 9/2000 | Lia et al. | |

* cited by examiner

Primary Examiner—Robert L Nasser
(74) Attorney, Agent, or Firm—Wall Marjama & Bilinski LLP

(57) ABSTRACT

A blood pressure measuring apparatus includes an inflatable cuff which can be wrapped about the limb of a patient. The sleeve includes a sealed interior capable of inflation, and an integrated inflation/measuring device. The integrated device is an elastomeric enclosure which retains a gage and a pneumatic bulb therein and hosing for fluidly interconnecting the pneumatic bulb, the inflatable cuff, and the gage.

17 Claims, 4 Drawing Sheets

HAND-HELD BLOOD PRESSURE MEASURING APPARATUS

FIELD OF THE INVENTION

This invention relates to the field of medical diagnostic instruments, and more particularly to a hand-held blood pressure measuring device.

BACKGROUND OF THE INVENTION

Typical blood pressure measuring instruments (ie., sphygmomanometers), such as the instrument 10 shown in FIG. 1, include an inflatable sleeve or cuff 14 which can be wrapped about a limb (e.g., an arm or leg—not shown) of a patient. The sleeve 14 is inflated by means of a pneumatic assembly 18 which includes a hose 23 permitting interconnection to a port 22 of the sleeve, thereby providing a fluid path to the interior of the sleeve 14.

A gage 26 is also separately tethered through a hose 27 to an adjacent port of the inflatable sleeve 14 and is in fluid communication with the interior of the sleeve, the housing including a dial face 30 which includes measuring indicia 32. A movement mechanism (not shown) provided within the interior of the gage 26 is responsive to changes in pressure of the sleeve interior and causes an attached indicating member to move relative to the measuring indicia 32 on the dial face 30 as the sleeve 14 is inflated and deflated using the pneumatic assembly 18. A stethoscope (not shown) is used to monitor the heartbeats of the brachial artery (when the sleeve 14 is wrapped onto a patient's arm) and to determine systolic and diastolic pressure of the patient using the gage 26 as the sleeve is inflated to an appropriate inflation pressure and then deflated using a bleed valve 36.

General efforts have been made to further incorporate features of sphygmomanometers together. One such apparatus 40, shown in FIGS. 2 and 3, incorporates a gage 44 having a pneumatic bulb 48 which is attached to the bottom of the gage 44 in a hand-held assembly. The combination device 40 is also fluidly connected through a hose 43, one end of which is attached to a port 47 provided in the gage 44, to the interior of an inflatable sleeve 45 (shown only in FIG. 2) and includes a trigger 54, (shown only in FIG. 3) which enables valving 56 (also shown only in FIG. 3) to permit deflation of the inflatable sleeve. This particular device, however, is relatively complex and includes a significant number of intricate parts between the bulb 48 and the gage 44 for successful operation.

SUMMARY OF THE INVENTION

It is a primary object of the present invention to overcome the above-noted deficiencies of the prior art.

It is a further primary object of the present invention to provide a blood pressure measuring apparatus which is more compact and easier to use than previously known apparatus.

It is yet another primary object to provide a blood pressure measuring apparatus which effectively combines a gage and a pneumatic inflation/deflation assembly.

Therefore, and according to a preferred aspect of the invention, there is provided a blood pressure measuring apparatus, said apparatus comprising:

an inflatable sleeve which can be wrapped about a limb of a patient;

a gage connected fluidly to the interior of said sleeve, said gage including a movement mechanism which is responsive to changes in pressure within said sleeve; and a pneumatic bulb fluidly connected to said sleeve for inflating the interior thereof, wherein said pneumatic bulb and said gage are each integrally retained within an elastomeric enclosure.

According to one version, an inflatable bladder is contained within the elastomeric enclosure and attached to valving which is also fluidly connected to the movement mechanism contained within the gage. The apparatus also includes a trigger which enables the release of air/fluid from the sleeve.

According to another version, the elastomeric sleeve itself can be used to inflate and deflate a blood pressure cuff.

For a further understanding of these and objects of the invention, reference will be made to the following Detailed Description which should be read in connection with the accompanying drawings.

DETAILED DESCRIPTION

The following discussion relates to certain embodiments of a combination blood pressure measuring apparatus. During this discussion, terms such as "top", "upper", "lower", "bottom," among others, are used in order to provide a frame of reference with regard to the accompanying drawings. These terms, however, are not intended to be limiting with regard to the inventive concepts as claimed herein.

Figure 1:
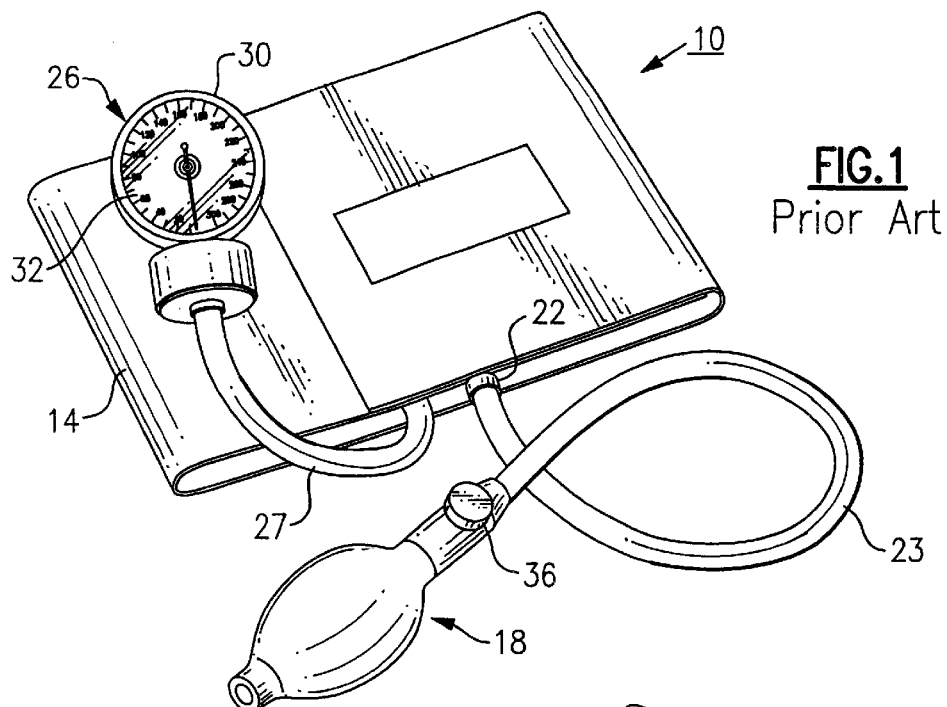
FIG. 1 is a top perspective view of a known blood pressure measuring apparatus.
Figure 2:
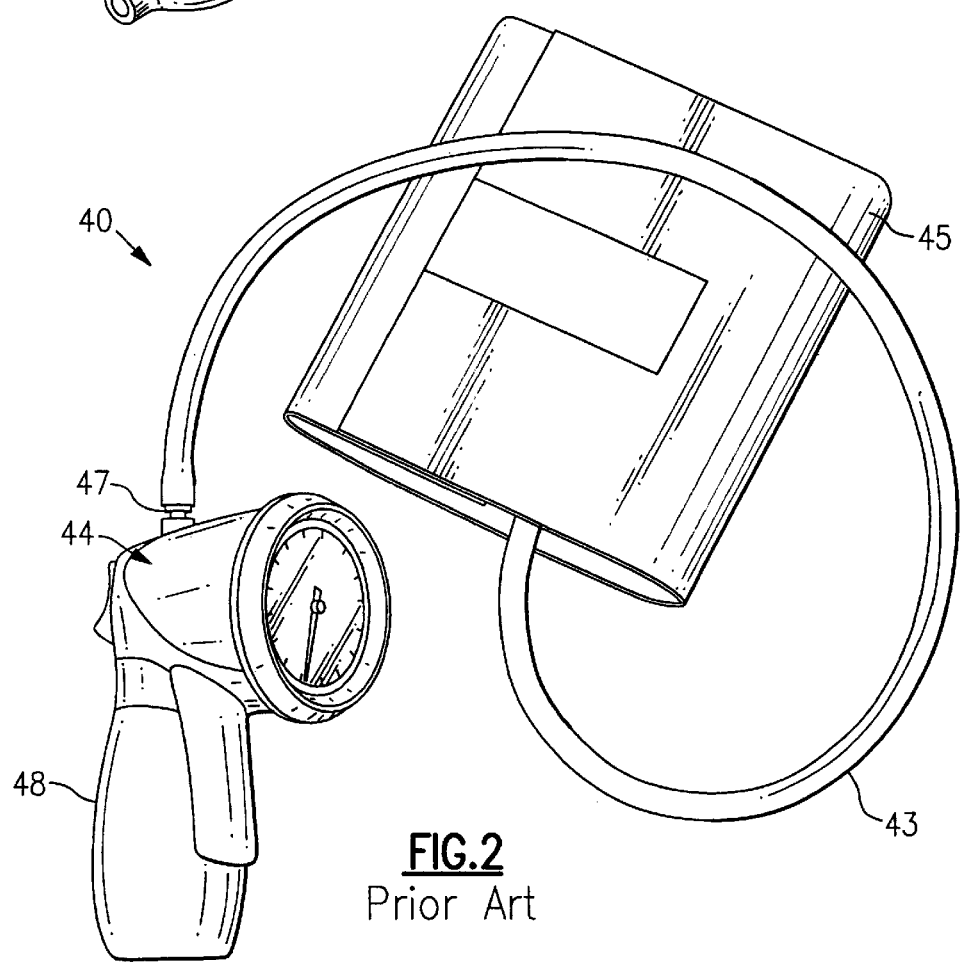
FIG. 2 is a top perspective view of another known blood pressure measuring apparatus.
Figure 3:
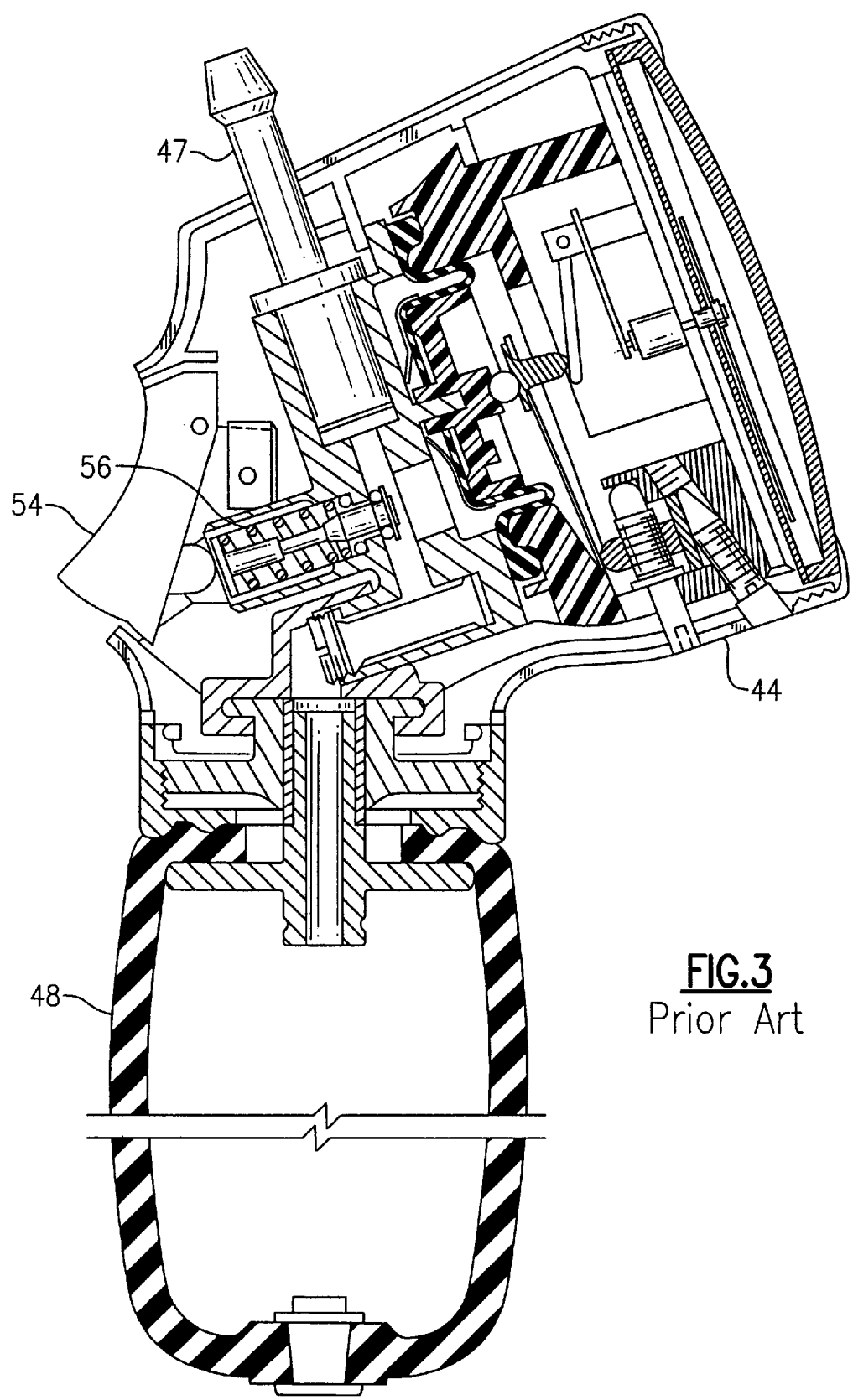
FIG. 3 is a front elevational view, shown in section, of a portion of the blood pressure measuring apparatus of FIG. 2.
Figure 4:
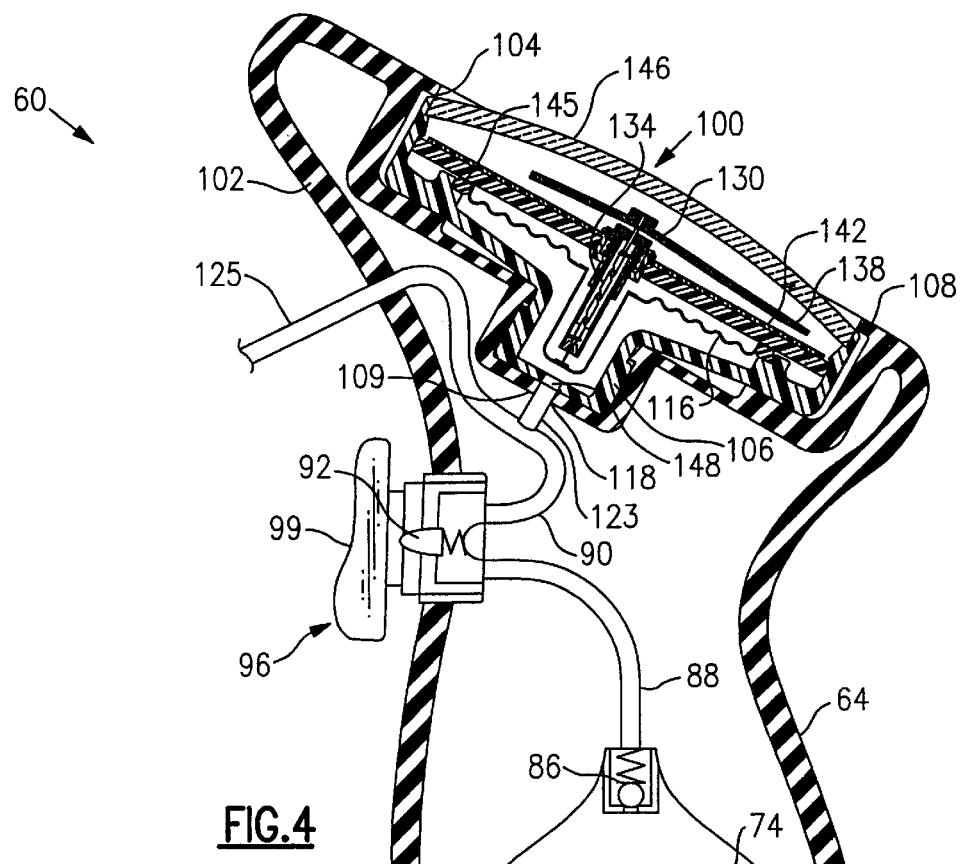
FIG. 4 is a partial side elevational view, shown in section, of a blood pressure measuring apparatus according to a first embodiment of the invention.

Referring to FIG. 4, there is shown a first version of an integrated blood pressure apparatus 60 that includes an elastomeric sleeve 64 which is sized and shaped to permit a lower portion 68 thereof to be hand-held. Preferably, the sleeve 64 is manufactured from a rotational moldable material, such as medical grade PVC, the sleeve being fluid impermeable. A flexible depressable bulb 72 is disposed within the lower portion 68 of the sleeve 64 which can be squeezed by the user. A lower portion 76 of the depressible bulb 72 includes a one-way valve 80 disposed in relation to an inlet port 84 disposed at the bottom of the sleeve 64. A second one-way valve 86 attached to an upper portion 74 of the depressable bulb 72 prevents air from reentering the bulb.

A hose 88 extends from the upper portion 74 of the bulb 72 to a trigger assembly 96. The trigger assembly 96 includes a bleed valve 92 which is connected to one end of the hose 88 extending from the depressible bulb as well as hose 90. The bleed valve 92 is engaged by an actuable trigger 99 which is biasedly attached thereto, the trigger projecting from the exterior of the elastomeric sleeve 64.

A gage 100 is sealingly retained within an upper portion 102 of the elastomeric sleeve 64, preferably within an opening or pocket 108 which is smaller in diameter than the diameter of the gage 100 so as to provide secure engagement therewith. The gage 100 is defined by a substantially cylindrical shaped body including an upper portion 104 and a lower engagement end 106. A movement mechanism contained within the gage 100 is responsive to pressure changes occurring within a fluidly interconnected inflatable sleeve (not shown) as described below.

Still referring to FIG. 4, the movement mechanism includes a diaphragm 116 which is horizontally arranged within the interior of the gage 100 having a movable surface. One end of a vertically arranged shaft member 130 is arranged in proximity to the movable surface of the diaphragm 116, the shaft member being supported for axial movement. A helical ribbon spring 134 is wrapped about a portion of the shaft member 130. One end of the spring 134 is attached to a fixed portion of the gage 100 and an opposite end of the spring is attached to an intermediate portion of the shaft member 130. An indicating member 138 is supported at the upper end of the shaft member 130 relative to a dial face 142 with indicia (not shown). A transparent window 146 covers the upper portion 102 of the gage 100.

The lower engagement portion 106 of the gage 100 includes a port 148 which permits air/fluid to enter the interior of the gage. A lower portion of the retaining pocket 108 includes an opening 118 which is connected to one end of a hose section 123 extending therefrom. The diaphragm 116 is sealingly mounted within the interior by means of an O-ring 145 to create a fluid-tight seal within the gage 100.

The hose 90 extending from the trigger assembly 96 splits into two sections 123, 125 at a T-section. Hose section 123 extends to the port 148 formed in the gage 100 through an aligned opening 109 in the retaining pocket 108 while hose section 125 extends from the device 60 to an inflatable sleeve (not shown).

In operation, the lower portion 68 of the elastomeric sleeve 64 is squeezed, thereby causing air to be drawn into the pneumatic bulb 72 through the one-way valve 80 and out of the top of the bulb through hose 88. The bleed valve 92 of the trigger assembly 96 is initially closed and therefore air is directed both to the interior of the inflatable sleeve (not shown) and the gage 100 through hose sections 123, 125 respectively. Air entering the gage 100 through opening 109 and port 148 causes movement of the diaphragm 116 as well as corresponding axial movement of the shaft member 130. As the shaft member 130 translates upwardly, the flexion of the helical wound spring 134 against the fixed support of the gage 100 causes the shaft member to rotate and cause corresponding movement of the indicating member 138 as well as relative to the indicia on the dial face 142. Additional details concerning the movement mechanism and the gage 100 are provided in U.S. Pat. No. 5,966,829, the entire contents of which are herein incorporated by reference.

Activation of the trigger 99 causes the bleed valve 92 to open, allowing deflation of the sleeve (not shown) and air to escape from the gage housing 100.

Figure 5:
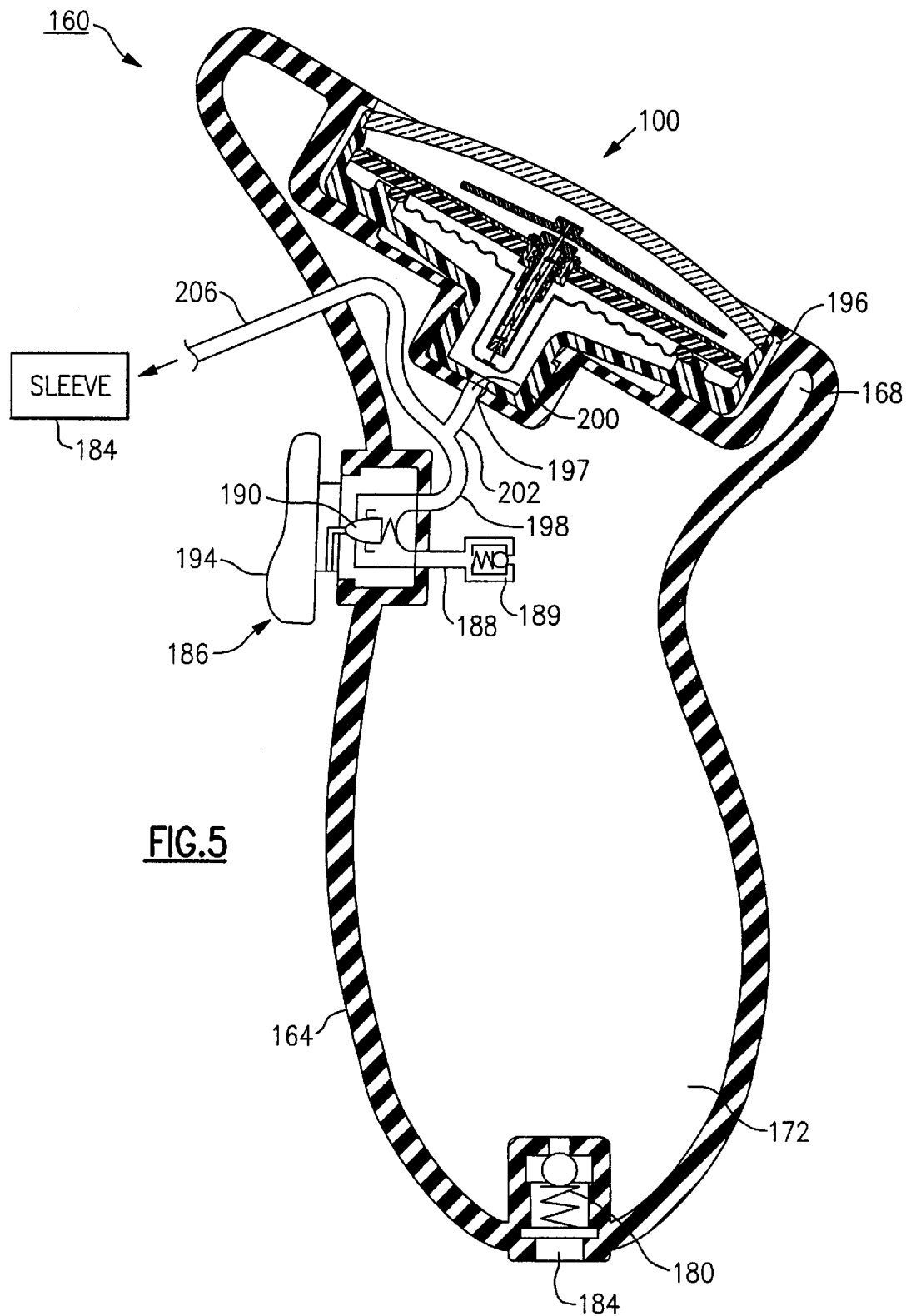
FIG. 5 is a partial side elevational view, shown partially in section, of a blood pressure measuring device according to a second embodiment of the invention.

According to FIG. 5, a second version of an integrated blood pressure measuring apparatus 160 includes an elastomeric or enclosure sleeve 164 similar in shape to the preceding and including an upper portion 168 and a contiguous lower portion 172. In lieu of providing a pneumatic bulb within the lower portion 172 of the elastomeric sleeve 164, the sleeve itself provides the means for pneumatically inflating a blood pressure cuff (shown diagrammatically as 184). A one way valve 180 provided at the bottom of the lower portion 172 of the sleeve 164 permits air to enter the interior of the sleeve when squeezed.

A trigger assembly 186 disposed along a wall of the sleeve 164 includes a bleed valve 190 which can be opened by means of an actuable trigger 194 provided on the exterior of the sleeve 164. The trigger 194 is biasedly connected to the bleed valve 190 through conventional means. A hose 188 extends into the trigger assembly 186, the hose including a valve 189 which permits air from the interior of the sleeve to pass into the hose 188. Another hose 198 extends from the trigger assembly 186, splitting into sections 202, 206 respectively. Section 206 extends from the device 160 to the sleeve 184 and is connected to a port (not shown) which is in fluid communication with the interior of the sleeve.

The sleeve 160 is similar to sleeve 60 described above and includes a retaining pocket 196 which is preferably smaller in diameter than that of the gage 100 to provide secure engagement with the exterior thereof. The gage 100 is identical to that previously described above including a movement mechanism, such as described by previously incorporated U.S. Pat. No. 5,966,829, which permits circumferential movement of an indicating member relative to a dial face. Hose section 202 extends to a port 200 provided in the retaining pocket 196 which provides a fluid path through port 148, FIG. 4, and an aligned opening 197 into the interior of the gage 100.

In operation, lower portion 172 of the sleeve 164 is squeezed permitting air to enter the interior of the sleeve and into hose 188 through check valve 189. Initially, the bleed valve 190 is closed, therefore air is directed through the trigger assembly 186 and through hose 198 and hose sections 202, 206 to the interior of the gage 100 and the sleeve 184, permitting inflation of the latter.

Air entering the interior of the gage 100 causes circumferential movement of the indicating member 138, FIG. 4, as previously described due to the movement mechanism, FIG. 4.

Opening of the bleed valve 190 is accomplished through use of the trigger 194 which permits deflation of the sleeve 184 whereupon a blood pressure measurement can be made.

Figure 6:
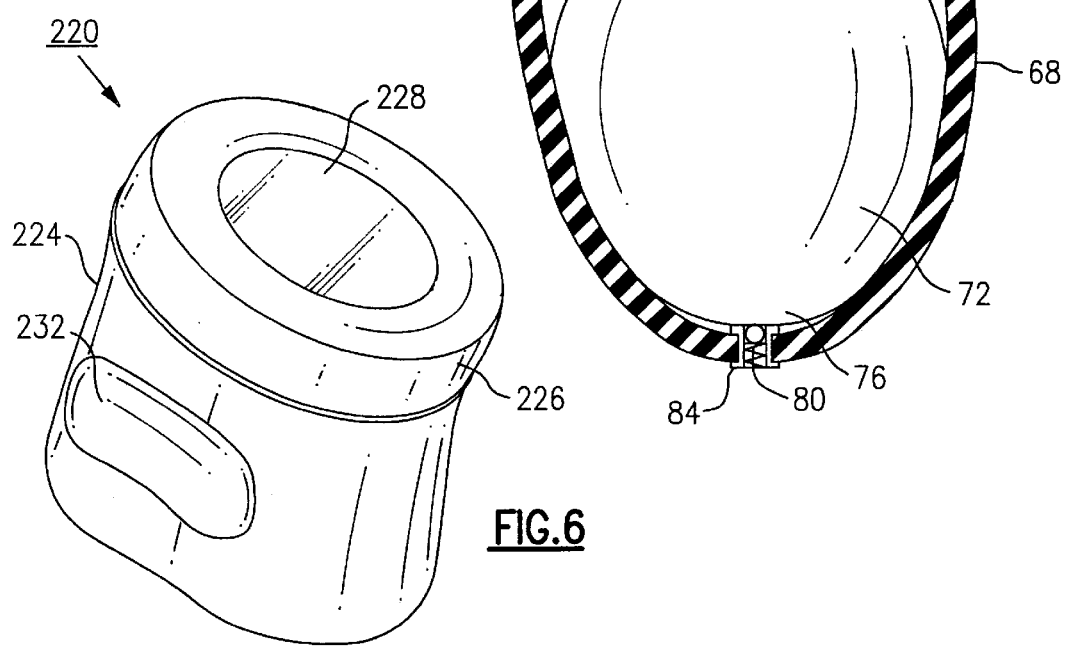
FIG. 6 is a top perspective view of a blood pressure measuring device made n accordance with a third embodiment of the invention.

Alternate designs incorporating the inventive concepts described herein are possible. For example, and referring to FIG. 6, a blood pressure measuring device 220 according to a third embodiment is shown. The device 220 is defined by a cylindrical sleeve 224 having an upper portion 226 which includes a retaining pocket 228 sized to sealingly engage a gage 100, FIG. 4, as previously described. The sleeve 224 includes lower squeeze portions 232 to enable a pneumatic function. Alternately, a pneumatic bulb (not shown) can be provided within the sleeve 224 to permit inflation of a connected sleeve.

PARTS LIST FOR FIGS. 1–6

10 blood pressure measuring instrument
14 inflatable sleeve or cuff
18 pneumatic assembly
22 port
23 hose
26 gage
27 hose
30 dial face
32 measuring indicia
36 bleed valve
40 apparatus
43 hose
44 gage
45 sleeve
47 port 48 pneumatic bulb
54 trigger
56 valving
60 blood pressure measuring device
64 elastomeric sleeve
68 lower portion—sleeve
72 bulb, depressible
74 upper portion—bulb
76 lower portion—bulb
80 one-way valve
84 inlet port
88 hose
90 hose
92 valve
96 trigger assembly
99 trigger
100 gage
102 upper portion—sleeve
104 upper portion—gage
106 lower engagement end
108 retaining pocket
109 opening
116 diaphragm
118 opening
122 hose
123 hose
125 hose
130 shaft member
134 helical ribbon spring
138 indicating member
142 dial face
145 O-ring
146 transparent window
148 port
160 blood pressure measuring apparatus
164 sleeve, elastomeric
168 upper portion
172 lower portion
180 one way valve
184 sleeve
186 trigger assembly
188 hose
189 check valve
190 bleed valve
194 trigger
196 pocket
197 opening
198 hose
200 port
202 hose
206 hose
220 blood pressure measurement device
224 elastomeric sleeve
226 upper portion
228 retaining pocket
232 squeeze portion While the present invention has been particularly shown and described with reference to the preferred mode as illustrated in the drawing, it will be understood by one skilled in the art that various changes in detail may be effected therein without departing from the spirit and scope of the invention as defined by the claims.

We claim:

1. A blood pressure measuring apparatus comprising:
an inflatable cuff which can be wrapped about the limb of a patient, said cuff including a sealed interior capable of inflation; and
an integrated inflation/pressure measuring device, said inflation/pressure measuring device including an elastomeric enclosure which retains a gage and a pneumatic bulb therein and means for fluidly interconnecting said pneumatic bulb, said inflatable cuff, and said gage wherein said gage comprises at least one pressure responsive member, a shaft member supported for axial movement having one end in substantial proximity to said at least one pressure responsive member and a helical ribbon spring wrapped about said shaft member, said one end of said helical ribbon spring attached to a fixed portion of said gage wherein changes in the inflated pressure of said cuff during blood pressure measurement cause deflection of said at least one pressure responsive member, causing shaft member to move axially, said ribbon spring to flex, and said shaft member to rotate to indicate the resulting change in pressure.

2. An apparatus as recited in claim 1, wherein said elastomeric enclosure includes a depressable portion which serves as said pneumatic bulb.

3. An apparatus as recited in claim 2, including a bleed valve for permitting deflation of said inflatable cuff.

4. An apparatus as recited in claim 3, including a trigger attached to said bleed valve for activating said bleed valve.

5. An apparatus as recited in claim 2, wherein said fluid interconnection means includes at least one hose extending between said depressable portion of said elastomeric sleeve, said inflatable cuff, and the interior of said gage.

6. An apparatus as recited in claim 2, wherein said gage is retained within a pocket of said elastomeric sleeve.

7. An apparatus as recited in claim 1, including a bleed valve for permitting deflation of said inflatable cuff.

8. An apparatus as recited in claim 7, including a trigger attached to said bleed valve for selectively activating said bleed valve.

9. An apparatus as recited in claim 7, including at least one bleed valve connected to said at least one hose.

10. An apparatus as recited in claim 1, wherein said fluid interconnection means includes at least one hose extending between said pneumatic bulb, said inflatable cuff, and the interior of said gage.

11. An apparatus as recited in claim 1, wherein said gage is retained within a pocket of said elastomeric sleeve.

12. An elastomeric sleeve for use in a blood pressure measuring device, said sleeve comprising:
a sleeve body;
an elastomeric pocket defined in an upper end of said sleeve body sized for substantially retaining a gage containing an axial movement mechanism; and
a depressable pneumatic portion in a lower end of said sleeve body, wherein said sleeve is capable of being hand-held and in which said depressable pneumatic portion is capable of inflating an attached blood pressure cuff;
in which said pocket is sized such that said gage is inset within the confines of said pocket.

13. An integrated inflation/blood pressure measuring device comprising:
an elastomeric enclosure which retains a gage and a pneumatic bulb therein; and
means for fluidly interconnecting said pneumatic bulb, said gage,
and an inflatable blood pressure cuff, wherein said gage includes at least one pressure responsive member, a shaft member having one end disposed in substantial proximity to said to said at least one pressure responsive member, said shaft member being supported for axial movement and a helical ribbon spring attached to said shaft member, one end of said ribbon spring being attached to a fixed portion of said gage such that changes in the inflated volume of an interconnected blood pressure cuff are imparted to said at least one pressure responsive member causing movement thereof, causing said shaft member to move axially, said ribbon spring to flex and said shaft member to rotate, said shaft member having indicating means attached to an opposing end.

14. A device as recited in claim 13, wherein the elastomeric enclosure includes an elastomeric pocket for retaining said gage.

15. A device as recited in claim 13, wherein a portion of said elastomeric enclosure serves as the pneumatic bulb.

16. A device as recited in claim 15, wherein said fluid interconnecting means includes at least one hose interconnecting said blood pressure cuff, said gage, and said pneumatic bulb of said elastomeric enclosure.

17. A device as recited in claim 13, wherein said fluid interconnecting means includes at least one hose interconnecting said blood pressure cuff, said gage and said pneumatic bulb.

* * * * *